United States Patent [19]

Inoue

[11] Patent Number: 4,825,365

[45] Date of Patent: Apr. 25, 1989

[54] MULTI-IMAGING APPARATUS

[75] Inventor: Akira Inoue, Otawara, Japan

[73] Assignee: Kabushiki Kaisha Toshiba, Kawasaki, Japan

[21] Appl. No.: 7,403

[22] Filed: Jan. 27, 1987

[30] Foreign Application Priority Data

Feb. 14, 1986 [JP] Japan .................................. 61-30180

[51] Int. Cl.⁴ .................... G06F 15/42; G01N 23/04; G03B 42/02
[52] U.S. Cl. ................................ 364/413.19; 364/518
[58] Field of Search ........................ 364/518, 521–522, 364/414; 340/724–725, 731, 751; 358/111

[56] References Cited

U.S. PATENT DOCUMENTS

| 4,030,119 | 6/1977 | Ellis | 358/11 |
|---|---|---|---|
| 4,079,417 | 3/1978 | Scudder, III | 358/111 |
| 4,559,533 | 12/1985 | Bass | 340/724 |
| 4,563,740 | 6/1986 | Blake | 364/414 |
| 4,590,559 | 5/1986 | Baldwin et al. | 364/414 |
| 4,602,333 | 7/1986 | Komori | 364/414 |
| 4,642,621 | 2/1987 | Nemoto | 340/724 |
| 4,700,320 | 10/1987 | Kapur | 364/521 |
| 4,755,954 | 7/1988 | Netter | 364/518 |

OTHER PUBLICATIONS

S. N. Hack et al, "Distributed Reading Station Network for Medical Images", IEEE Frontiers of Engineering and Computing in Health Care, 1984.

Primary Examiner—Jerry Smith
Assistant Examiner—Gail O. Hayes
Attorney, Agent, or Firm—Oblon, Fisher, Spivak, McClelland & Maier

[57] ABSTRACT

A multi-imaging apparatus for photographing, on a multi-image film, a group of images produced from data collected by a medical diagnostic system such as a CT scanner. The images displayed on a monitor can be successively photographed on the multi-image film by a camera unit with automatic windowing control. It is not necessary for the operator to register monitoring conditions such as a window level and a window width each time an image is to be photographed in a film frame.

2 Claims, 2 Drawing Sheets

MULTI-IMAGING APPARATUS

BACKGROUND OF THE INVENTION

The present invention relates to a multi-imaging apparatus for photographing, on a multi-image film, a group of images derived from data collected by a medical diagnostic system such as a CT (Computerized Tomographic) scanning apparatus.

Generally, a group of images obtained from a CT scanning apparatus, e.g., a number of tomographic images of sections or "slices" of a patient, are photographed and arranged in imaging or slicing order on a multi-image film so that the slice images can be observed at the same time. For preparing such a multi-image film, it is current practice for the operator to display images to be photographed, successively on a monitor, then to set monitoring conditions such as window level/width for each frame or image, and subsequently to photograph the image with a multiformat camera.

The conventional process of preparing multi-image films is however disadvantageous in that the operation is very complex and inefficient especially when photographing one multi-image format on a plurality of films since each image must be specified and photographing conditions must be set for each image in the same manner for second, third and any successive films as done for the first film.

SUMMARY OF THE INVENTION

In view of the aforesaid shortcomings of the conventional multi-imaging apparatus, it is an object of the present invention to provide a multi-imaging apparatus capable of photographing a group of images on a multi-image film without setting monitoring conditions again, for thereby reducing the expenditure of labor in producing the multi-image film.

According to the present invention, the above object can be achieved by a multi-imaging apparatus comprising monitor means for displaying an image based on image data of an object which is collected by a medical diagnostic system, a window circuit for windowing the image displayed on the monitor means, a camera unit for photographing the image displayed on the monitor means in an area of a multi-image film having a plurality of photographing areas, a memory for storing data of the displayed image in association with window condition data for the image and image identifying data, and a processor for controlling the storage of the data into the memory.

The above and other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Figure 1:
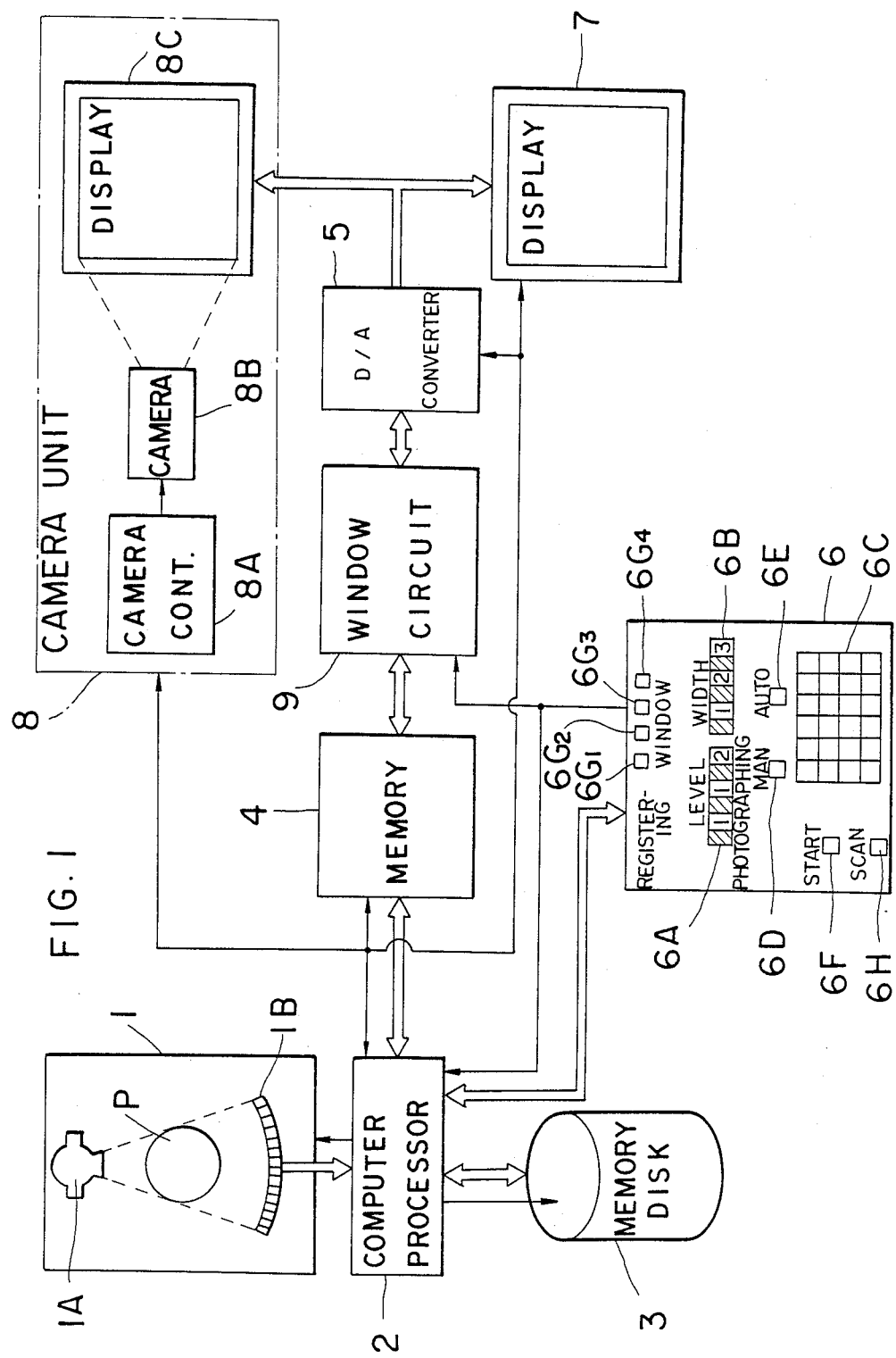
FIG. 1 is a block diagram of a multi-imaging apparatus according to the present invention.

FIG. 1 shows a multi-imaging apparatus according to the present invention, incorporated in a CT scanner designated by the reference numeral 1. The CT scanner 1 has an X-ray tube 1A and an X-ray detector 1B which are disposed in confronting relation with an object P therebetween. When the X-ray tube 1A and the X-ray detector 1B revolve around the object P, information derived from X-rays that have passed through the object P is generated by the detector 1B. A computer processor 2 which includes a CPU (Central Processing Unit) as a control processor serves to analyze scanned data from the CT scanner 1, reconstruct an image, issue image data, and control various blocks (described later). The image data produced by the computer processor 2 is stored in and read out of a memory disk 3. A memory 4 stores, under the control of the computer processor 2, one frame of the image data stored in the memory disk 3. The image data stored in the memory 4 can be read therefrom under the control of the CPU and converted into analog image data through a window circuit 9 and a D/A (digital-to-analog) converter 5 for simultaneous display on observation and photographing display units or monitors 7, 8C.

An input unit 6 includes a panel having various keys and dials. More specifically, the panel has a window level setting dial 6A, a window width setting dial 6B, a group of numerical keys (ten keys) 6C, a manual setting key 6D for photographing operation, an automatic setting key 6E for photographing operation, a starting key 6F, and setting keys 6G1 through 6G4 for registering operation. The setting key 6G1 is used for registering a window, the setting key 6G2 for registering a slice number, the setting key 6G3 for registering a film number, and the setting key 6G4 for registering a frame position. Various items of image identifying information such as the name and number of the patient can be specified by the numerical keys 6C. Window conditions as monitoring conditions can be set by operating the dials 6A, 6B. Photographing conditions such as a film number, a slice number (a frame position number in multiformat), and the number of slice images to be photographed on the same film can be set by depressing either the manual setting key 6D or the automatic setting key 6E, then depressing the corresponding ones of the registering keys 6G, and thereafter entering input information through the numerical keys 6C. The set data from the input unit 6 are delivered to the CPU in the computer processor 2. Particularly, the window conditions are also applied via a control line to the window circuit 9 in which a window is established on the basis of the delivered window conditions. The panel of the input unit 6 also includes a scanning key 6H for effecting scanning operation in the CT scanner 1.

A camera unit 8 includes a camera controller 8A, a camera 8B, and the display unit 8C. The camera unit 8 is responsive to a control signal from the computer processor 2 for photographing the image displayed on the display unit 8C.

Figure 2:
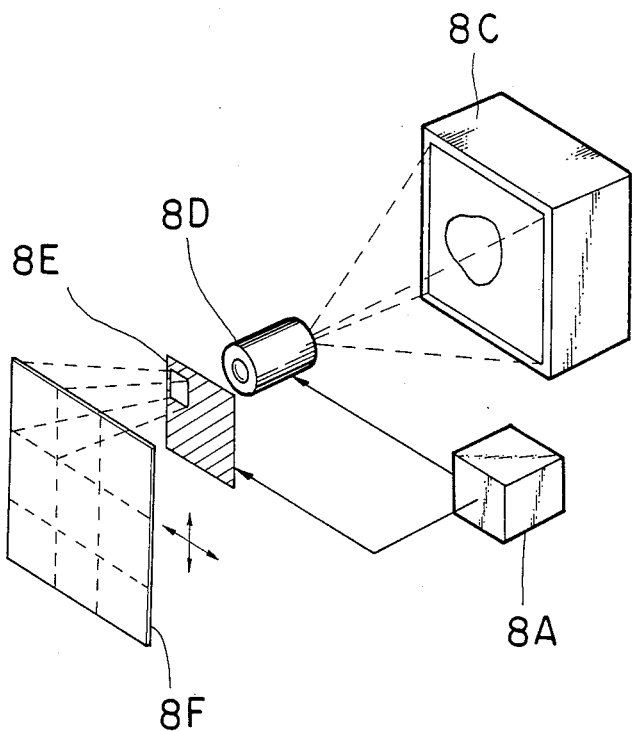
FIG. 2 is a schematic perspective view of a camera unit employed in the multi-imaging apparatus.

FIG. 2 shows a specific arrangement of the camera unit 8. The camera unit 8 has a lens unit 8D positioned in front of the display unit 8C, and a filter 8E disposed behind the lens unit 8D. A multi-image film 8F is disposed behind the filter 8E. The lens unit 8D has a shutter therein which is actuatable in response to a control signal from the camera controller 8A. The filter 8E is also responsive to the control signal for moving in one of the directions indicated by the arrows to bring a slit into alignment with one frame on the multi-image film 8F. The image displayed on the display unit 8C can then be photographed on that frame of the film 8F.

The control processor or CPU in the computer processor 2 is programmed to sequentially operate the various blocks shown in FIG. 1. The CPU operates selectively in a registering mode in which the window conditions for an image to be displayed are registered in the memory in association with image identifying information according to instructions from the input unit 6, and a photographing mode in which the image is displayed according to the registered conditions and then photographed. More specifically, when the starting key 6F is depressed and image identifying information such as the name and number of a patient is entered via the numerical keys 6C, the CPU in the computer processor 2 is operated to successively read a group of stored section or slice images of the patient from the memory disk 3 into the memory 4, and to store information on the specified conditions from the input unit 6 into the memory disk 3 in association with the image data read into the memory 4. Operation of the camera unit 8 is controlled by the photographing key 6D or 6E.

Operation of the multi-imaging apparatus of the above arrangement will be described below.

A group of images to be photographed on a multi-image film is registered together with image identifying information and photographing conditions as follows:

By depressing the scanning key 6H on the input unit 6, the CT scanner 1 starts operating, and data derived by an X-ray beam that has passed through a certain slice position of a patient P is entered into the computer processor 2. The data is then processed by the computer processor 2 into image data, which is stored in the memory 4. The image data in the memory 4 is delivered via the window circuit 9 to the D/A Converter 5, which converts the received data to analog data that is displayed simultaneously on the display units 7, 8C.

The operator now observes the image displayed on the display unit 7 and operates the window level dial 6A and the window width dial 6B to adjust the displayed image so that the image will be optimized for being photographed. After the image adjustment, the window registering key 6G1 is depressed to enable the computer processor 2 to store the window condition data at this time into the memory disk 3 in association with the data of the image which is being displayed. Then, the slice number registrating key 6G2 and the numerical keys 6C are operated to set a slice number, the film number registering key 6G3 and the numerical keys 6C are operated to set a film number, and the frame position registrating key 6G4 and the numerical key 6C are operated to set a frame position on the multi-image film. These data items are delivered to the computer processor 2 and stored in the memory disk 3 in association with the displayed image data. When the above data items are stored in the memory disk 3, they are also associated with the image identifying information such as the patient's name.

The above process is repeated to successively store slice image data in association with identification data, window conditions, and photographing conditions for each scanning cycle. The registering operation is now completed.

Figure 3:
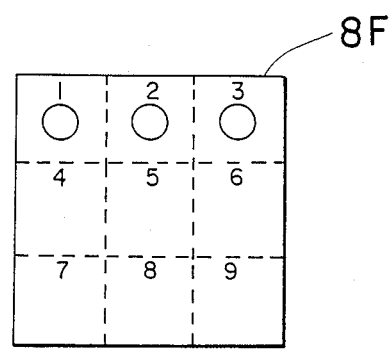
FIG. 3 is a front elevational view of a multi-format film.

Photographing operation is as follows:

A process of photographing an image is initiated by depressing the manual photographing key 6D. After the manual key 6D has been depressed, the numerical keys 6C are depressed to enter various specified data such as the name and number of a patient, a slice number, a film number, and a frame position, and the starting key 6F is depressed to enable the computer processor 2 to read the identified image from the memory disk 3 and deliver the image via the memory 4, the window circuit 9, and the D/A converter 5 to the display units 7, 8C on which the image is simultaneously displayed. Since the window condition data is associated with the image data at this time, the computer processor 2 controls the window circuit 9 based on the window condition data. Therefore, the display units 7, 8C automatically display the image that has been optimally windowed. The camera unit 8 is now controlled to photograph the image displayed on the display unit 8C in a specified frame position (for example, frame 1 in FIG. 3) on the first film 8F. The above process is repeated to photograph successive slide images on frames 2 through 9 of the film 8F. Inasmuch as the images to be photographed are automatically windowed, it is not necessary to provide a window setting each time an image is photographed.

Automatic successive photographing operation can be carried out as follows:

After the automatic photographing key 6E of the input unit 6 has been depressed, the numerical keys 6C are operated to enter the name and number of a desired patient, a film number, and slice numbers (for example, 9) to be photographed, and then to associate the slice numbers with frame positions. Thereafter, the starting key 6F is depressed to photograph the images successively based on the above specified settings, so that the slice images can automatically be photographed respectively in nine frames on one film. It is not necessary for the operator to give manual window settings since the window conditions for each frame are automatically set.

With the present invention, as described above, a group of images can be photographed on a multi-image film simply by specifying those images, without setting window conditions each time one image is to be photographed as has been required heretofore. Consequently, the large expenditure of labor which has conventionally been needed in producing multi-image films is greatly reduced, thus improving the photographing efficiency. Another advantage is that multi-image films of uniform quality can easily be produced even by an operator who is not specially trained or experienced.

Images that can be photographed by the multi-imaging apparatus of the present invention are not limited to CT scanned images, but may be images produced by gamma radiation, images produced by MRI (Magnetic Resonance Imaging), and the like.

Although a certain preferred embodiment has been shown and described, it should be understood that many changes and modifications may be made therein without departing from the scope of the appended claims.

I claim:

1. A multi-imaging apparatus comprising:
   an image displaying memory for storing image data of an object acquired by a medical diagnostic appliance;
   a monitor means for displaying the image data of said image displaying memory;

a window circuit having a plurality of window conditions, for windowing the image displayed by said monitor means;

a memory disk for storing the image data of said image displaying memory;

a camera unit for photographing the image displayed by said monitor in a portion of a multi-image film having a plurality of photographing areas;

an input means for selectively inputting said window conditions and image identifying data; and a computer processor for selectively controlling a registermode in which the window condition data selected by said input means is registered in association with the image identifying data while said acquired data is stored into said memory disk, an window-condition displaying mode in which the window conditions based on said registered window condition data are automatically selected and said monitor means displays a correspondingly windowed image for photographing by said camera unit, a photographing mode in which the operation of said camera unit is controlled.

2. A multi-imaging apparatus according to claim 1, wherein said monitor means includes an observation display unit and a photographing display unit for simultaneously displaying the image.

* * * * *